United States Patent
Fischer et al.

(10) Patent No.: US 12,208,253 B2
(45) Date of Patent: Jan. 28, 2025

(54) DEVICE FOR THE NEEDLE TUBE OF A SYRINGE

(71) Applicants: Stephan Fischer, Hiddenhausen (DE); Tobias Wilke, Ibbenbüren (DE); Bernd Mohr, Barmstedt (DE)

(72) Inventors: Stephan Fischer, Hiddenhausen (DE); Tobias Wilke, Ibbenbüren (DE); Bernd Mohr, Barmstedt (DE)

( * ) Notice: Subject to any disclaimer, the term of this patent is extended or adjusted under 35 U.S.C. 154(b) by 892 days.

(21) Appl. No.: 17/415,358

(22) PCT Filed: Oct. 28, 2019

(86) PCT No.: PCT/EP2019/079383
§ 371 (c)(1),
(2) Date: Jun. 17, 2021

(87) PCT Pub. No.: WO2020/126176
PCT Pub. Date: Jun. 25, 2020

(65) Prior Publication Data
US 2022/0062561 A1   Mar. 3, 2022

(30) Foreign Application Priority Data

Dec. 18, 2018   (DE) .................... 20 2018 107 232.3

(51) Int. Cl.
*A61M 5/32*   (2006.01)
*A61M 5/24*   (2006.01)
(Continued)

(52) U.S. Cl.
CPC ............ *A61M 5/3243* (2013.01); *A61M 5/24* (2013.01); *A61M 5/28* (2013.01); *A61M 5/3202* (2013.01);
(Continued)

(58) Field of Classification Search
CPC .... A61M 5/3243; A61M 5/28; A61M 5/3216; A61M 5/3271; A61M 5/3293;
(Continued)

(56) References Cited

U.S. PATENT DOCUMENTS 4,976,701 A    12/1990 Ejlersen et al.
5,342,322 A *  8/1994 Nathan ............... A61M 5/3216
                                                   604/263

(Continued)

FOREIGN PATENT DOCUMENTS

GB        2532979 A    6/2016

OTHER PUBLICATIONS

International Search Report (Jan. 3, 2020) for corresponding International App. PCT/EP2019/079383.

*Primary Examiner* — Tasnim Mehjabin Ahmed
(74) *Attorney, Agent, or Firm* — WRB-IP PLLC

(57) ABSTRACT

A device for the needle tube of a syringe includes a housing which can pivot on a carrier element for the needle tube and which has an open housing side in the pivoting plane of the housing such that the needle tube can be swung into the housing in order to be held there after being used for injection. The arrangement of the rear free end of the needle tube in the carrier element enables controlled piercing of the all of a container that is replaceable in the carrier element.

7 Claims, 5 Drawing Sheets

(51) Int. Cl.
*A61M 5/28* (2006.01)
*A61M 5/34* (2006.01)
*A61M 5/31* (2006.01)

(52) U.S. Cl.
CPC ........ *A61M 5/3216* (2013.01); *A61M 5/3271* (2013.01); *A61M 5/3293* (2013.01); *A61M 5/34* (2013.01); *A61M 2005/2474* (2013.01); *A61M 2005/3131* (2013.01)

(58) Field of Classification Search
CPC ...... A61M 5/24; A61M 5/3202; A61M 5/321; A61M 5/34; A61M 5/344; A61M 2005/2474; A61M 2005/3131
See application file for complete search history.

(56) References Cited

U.S. PATENT DOCUMENTS

2014/0135713 A1 5/2014 Domonkos
2018/0344934 A1* 12/2018 Schader .............. A61M 5/3202

* cited by examiner

DEVICE FOR THE NEEDLE TUBE OF A SYRINGE

BACKGROUND AND SUMMARY

The invention relates to a device for the needle tube of a syringe, comprising a housing, which can pivot on a carrier element for the needle tube and which has an open housing side in the pivoting plane of the housing such that the needle tube can be swung into the housing in order to be held there after being used for injection.

It is known that the needle of an injection syringe comprises a metal tube connected to a hollow carrier element provided with a syringe, which is connected to the cylindrical body of a syringe. The present invention has as its starting point a metal tube protection against needle sticks, particularly after an injection has been performed into the body of a patient. The purpose is to avoid infections on bodies that may come into contact with the needle after treatment. So, if a second person would be pricked with needles after it was used on a first person, it can lead to the transmission of diseases. Therefore, there is a considerable risk associated with the use of this needle, particularly hospital and medical staff for those who normally work with them, particularly hospital and medical staff. Disposing of used needles as waste also poses a hazard to those who handle or approach the waste containers. Therefore, the device for the needle tube has a housing pivotally formed on a carrier element, such that, after use of the needle tube, it can be pivoted back into the housing for protection.

The invention, according to an aspect thereof, is based in particular on the carrier element, wherein the outlet nozzle of a syringe, for example, is attached to the carrier element or to the needle tube in order to car out the infusion process by operating the plunger of the syringe. However, it is increasingly desired that, for example, so-called vials or containers in which the injection agent is held are also connected to the device in order to hold an injection in this way.

It is desirable to further develop a device for the needle tube of a syringe, which comprises a carrier element with a pivotably designed housing which is suitable for holding vial containers or other containers containing substances in such a way that they can be securely docked onto the carrier element.

The advantages achieved with an aspect of the invention are that the device according to an aspect of the invention for the needle tube of a syringe has a carrier element into which the spigot of a vial can be inserted in such a way that, on the one hand, safe docking and, on the other hand, safe withdrawal of the liquid through the needle tube can be performed.

According to an aspect of the invention, the arrangement of the free end of the needle tube in the carrier element enables controlled piercing of the wall of a container that can be inserted in the carrier element, if the container in the form of a vial is inserted into the carrier element, the container is automatically tapped to withdraw the injection fluid.

In a further development, the controlled piercing by the free end of the needle tube is effected by a pivoting or rotating movement of the inserted container relative to the carrier element. This configuration now makes it possible, if the spigot of the container is securely inserted in the carrier element, to perform an operation in the form of a pivoting movement or a rotary movement to safely tap the container without the injection liquid escaping through a leak.

The carrier element comprises a housing in which a rotatably mounted axially displaceable inner part is arranged. In a further development, the inner part is operatively connected to the housing via a slide guide. The controlled and targeted tapping process is carried out due to this configuration of the slide guide. This is achieved in that the slide guide comprises a sliding track running under an inclination in the housing wall, in which track a pin engages which is molded onto the wall of the inner part. Thus, if the attached container is rotated relative to the carrier element which has docked into the inner part, there is a movement of the inner part in the axial direction of the integrated needle tube, wherein the path traveled is sufficient to particularly pierce the wall of the container or the spigot.

The configuration and design of the inner parts such that the inner part has a sleeve-like receptacle in the upper region for the extraction region of the container. According to a particular embodiment, guides for the extraction area of the container are provided in the sleeve-like receptacle to ensure limited insertion of the container into the carrier element to prevent unintentional tapping of the container.

In this case, the extraction area of the container is designed as a cylindrical spigot, whereby a cap with a membrane provided at the bottom can be placed on the spigot, which membrane locks into the sleeve-like receptacle in the inserted state.

It is now possible that the vial with its spigot-like outlet is first provided with the cap, which is then inserted into the carrier element in such a manner that it latches onto the inner part in the extraction area. This results in a secure hold of the spigot on the one hand and a secure hold of the cap in the inner part on the other.

The inner part as such has another receptacle in the lower area for integrating the hub of the needle tube. In this case, the hub integration is held in detent positions in the receptacle. This configuration now makes it possible, when the inner part is displaced by the displacement path using the slide guide in the axial direction of the needle tube, that the needle tube end is brought into a final detent position wider counter pressure, such that the needle pierces or punctures the container in this final detent position.

BRIEF DESCRIPTION OF THE DRAWINGS

The figures show an exemplary embodiment of the invention that is explained in more detail below. Wherein.

DETAILED DESCRIPTION

Figure 1:
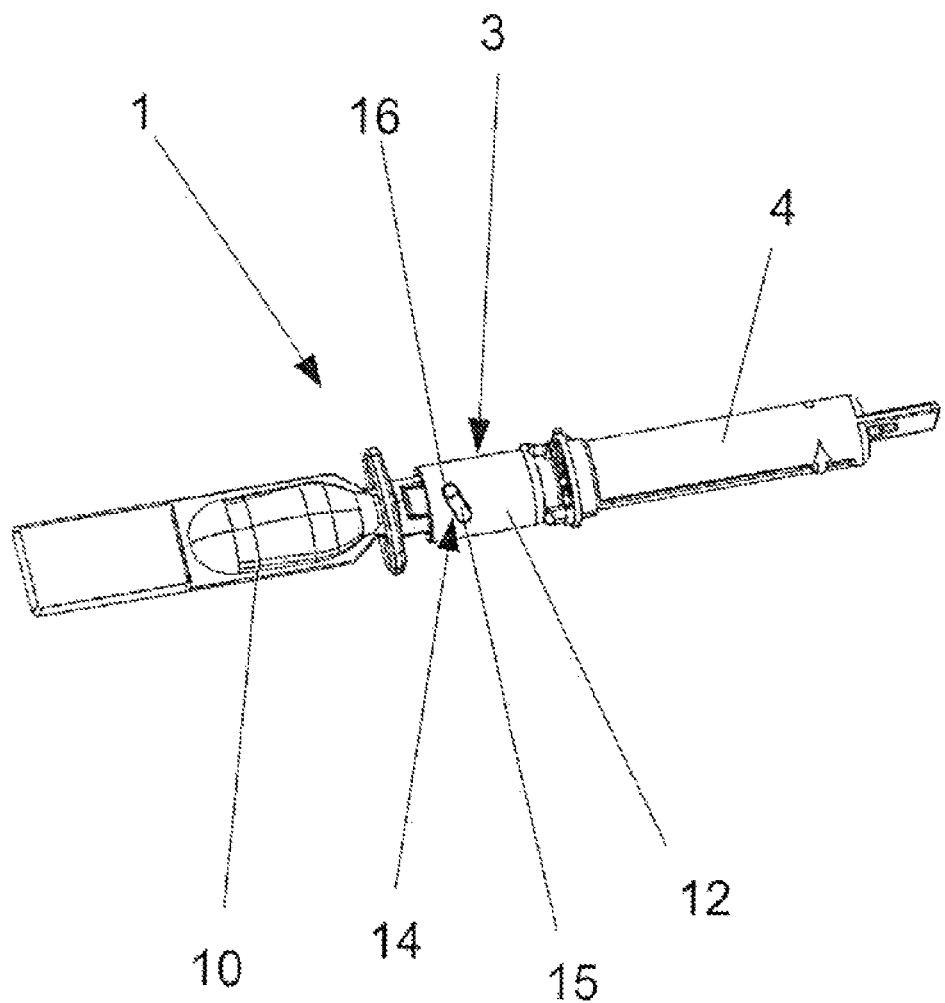
FIG. 1: shows a perspective side view of the device with attached vial.
Figure 2:
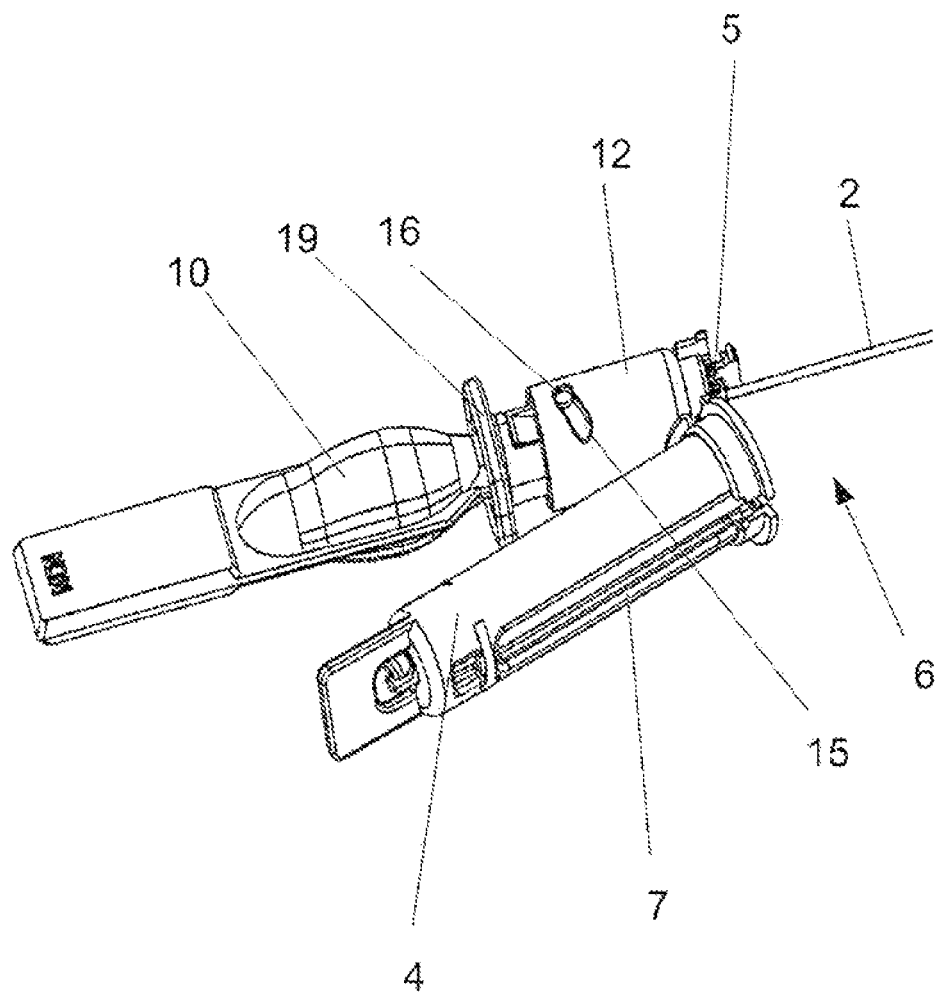
FIG. 2: shows another view according to FIG. 1 of the device with pivoted protective housing.

FIGS. 1 and 2 each show in different states a device 1 for the needle tube 2 of a syringe, which comprises a housing 4 pivotably formed on a carrier element 3 for the needle tube 2. As can particular be seen in FIG. 2, the housing 4 can be pivoted about a pivot axis 5 relative to a carrier element 3, such that the needle tube 2 is exposed for injection. The housing 4 has an open housing side 7 in the pivoting plane 6 of the housing 4, such that the needle tube 2 can be pivoted into the housing 4 after injection use, as documented in FIG. 1.

Figure 3:
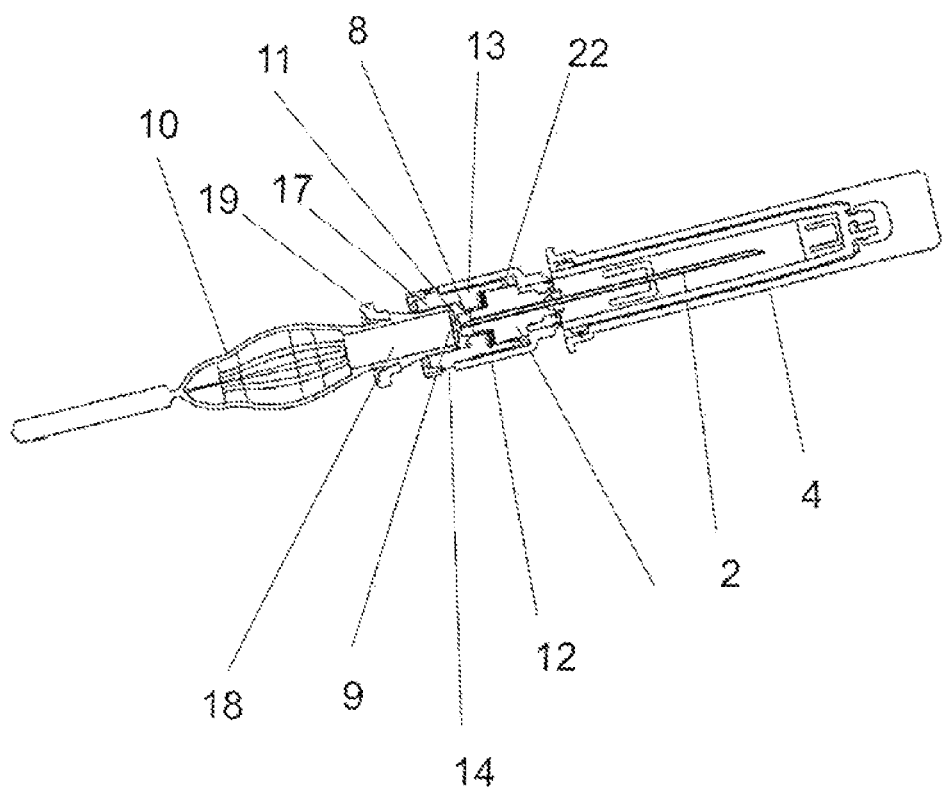
FIG. 3: shows a sectional side view of the device when the needle has not penetrated.
Figure 4:
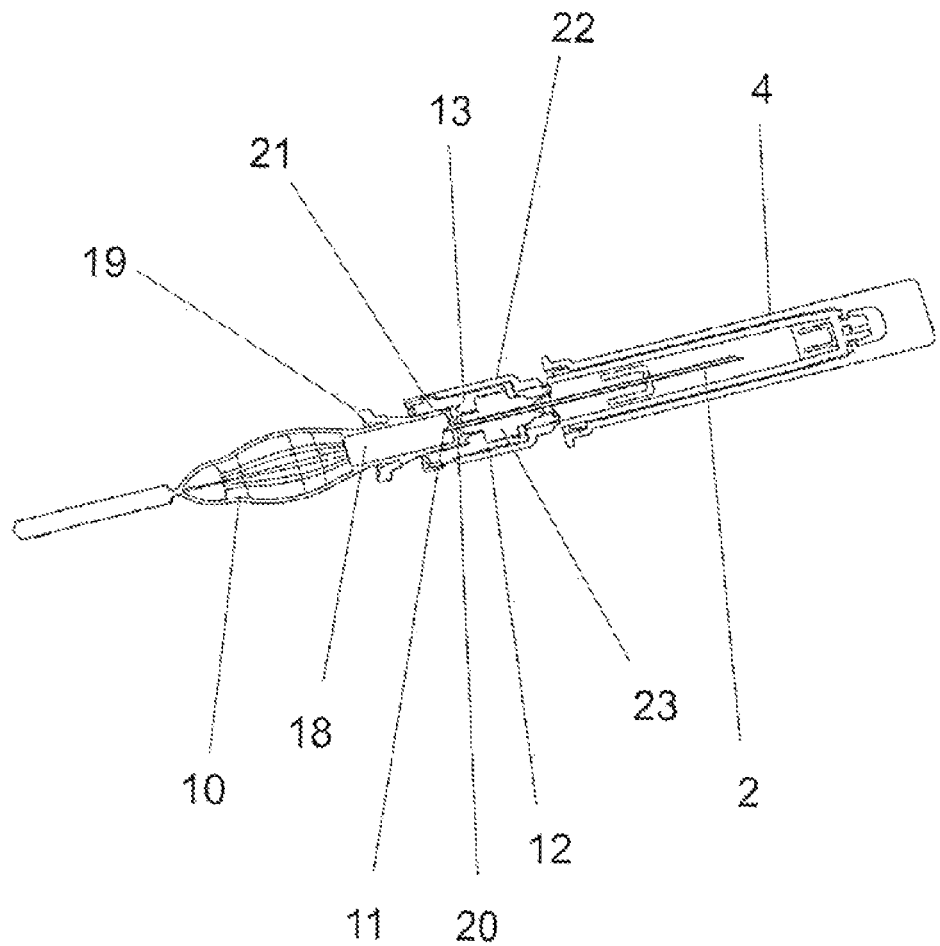
FIG. 4: shows another sectional view according to FIG. 3 when the needle has penetrated.
Figure 5:
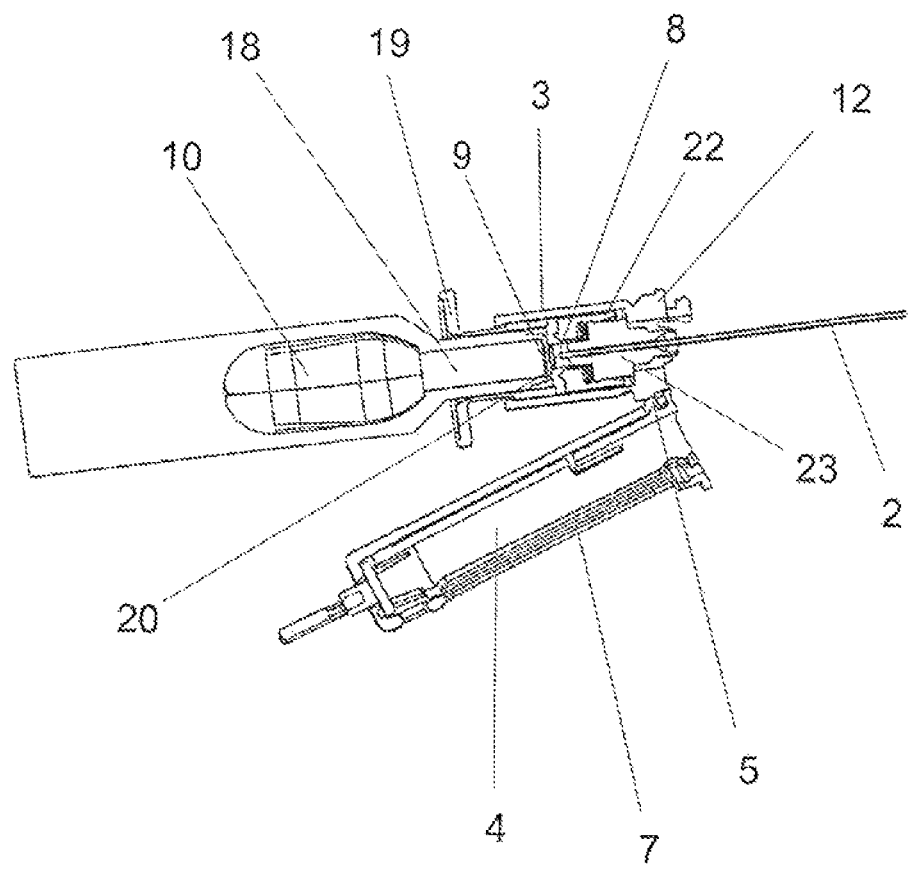
FIG. 5: shows another embodiment according to the invention with the housing pivoted off.

As can be seen from FIGS. 1 and 2, in this case the rear free end 8 of the needle tube 2 in the carrier element 3 is arranged in such a manner as to allow controlled piercing of the wall 9 of a container 10 inserted in the carrier element 3, as documented in the condition in FIG. 4. There it can be seen that the needle tube tip 11, which is slightly beveled, has penetrated into the container 10. The process of penetration or tapping is achieved here in that the rear free end 8 of the needle tube 2 by the pivoting and rotating movement of the inserted container 10 relative to the carrier element 3. To make this possible, the carrier element 3 comprises a housing 12 in which an inner part 13 is arranged, which is rotatably mounted and can be displaced therein. This can be seen particularly in FIGS. 3 and 4, and also in FIG. 5.

The inner part 13 is in operative connection with the housing 12 via a slide guide 14, as can be seen in more detail in FIGS. 1 and 2. The slide guide 14 comprises a sliding track 15 running under an inclination in the housing wall in which track a pin 16 engages which is molded onto the wall of the inner part 13. It will be appreciated, looking at the side view of FIG. 1, that if the housing 12 of the carrier element 3 is rotated or pivoted relative to the container 10, the pin 16 is guided accordingly in the sliding track 15, whereby a controlled operation of the inner part 13 in the housing 12 takes place, such that the attached container 10 travels along a displacement path into the carrier element 3.

If the path of the sliding, track 15 is traversed, the situation of FIG. 4 results, where particularly rear free end 8 of the needle tube 2 penetrates the wall 9 of the container 10. In this situation, the vial can be emptied such that the liquid held therein can be injected through the needle tube 2 from the vial configured as a container 10.

In another embodiment, the inner part 13, which is rotatable and displaceably mounted in the housing 12, has a sleeve-like receptacle 17 in the upper region for the extraction area of the container 10. The extraction area of the container 10 is configured here as a cylindrical spigot 18. According to a particular embodiment, guides for the extraction area of the container 10 are provided in the sleeve-like receptacle 17 to ensure limited insertion of the container 10 into the carrier element 3 to prevent unintentional tapping of the container 10.

As can be seen in particular from the synopsis of FIGS. 3 and 4, a cap 19 with a diaphragm 20 provided at the bottom is placed on the nozzle 18, which is inserted in the sleeve-like receptacle 17 and locked in place when inserted. The individual detents 21 are indicated in FIGS. 3 and 4 such that a secure connection is ensured as a result of the attached cap 19, particularly a connection of the socket 18 to the carrier element 3.

As can further be seen particularly from both. FIGS. 3 and 4, the inner part 13 has a lower receptacle 22 in the lower region for the hub integration 23 of the needle tube 2. In this case, the hub integration 23 is engaged in detent positions in the receptacle 22, wherein the hub integration 23 directly and firmly abuts in the receptacle 22 of the inner part 13, particularly in the second detent position, such that, as a result, safe penetration through the wall 9 takes place in the end position of the hub integration 23. The deem positions shown in FIGS. 3 and 4 correspond to the displacement of the inner part 13 in the housing 12 of the carrier element 3 when the sliding guide 14 is operated.

LIST OF REFERENCE NUMERALS 1 device
2 needle tube
3 carrier element
4 housing
5 pivoting axis
6 pivoting plane
7 open housing side
8 free rear end
9 wall
10 container
11 needle tube tip
12 housing carder element
13 interior
14 slide guide
15 sliding track
16 molded-on pin
17 receptacle
18 container spigot
19 cap
20 membrane
21 detents
22 lower receptacle
23 hub integration

The invention claimed is:

1. A device for a needle tube of a syringe, comprising a housing configured for pivoting on a carrier element for the needle tube, wherein the housing has an open housing side in a pivoting plane of the housing, such that the needle tube can be swung into the housing in order to be held there after being used for injection,
   wherein the carrier element comprises a carrier housing in which an inner part is arranged so as to be rotatably displaceable,
   wherein the inner part is operatively connected to the carrier housing via a slide guide,
   wherein the slide guide in a wall of the carrier housing comprises an obliquely extending sliding track in which a pin engages, the pin being molded onto a wall of the inner part, such that a rotary movement of an attached container docked in the inner part relative to the carrier element results in a movement of the inner part in the axial direction of the integrated needle tube,
   wherein the arrangement of a rear free end of the needle tube in the carrier element as a result of the path traveled of the inner part due to the rotational movement of the container allows controlled piercing of the wall of the container.

2. The device according to claim 1, wherein the inner part has a sleeve-like receptacle in an upper region for an extraction area of the container.

3. The device according to claim 1, wherein guides for an extraction area of the container are provided in a sleeve-like receptacle, which ensure a limited insertion.

4. The device according to claim 1, wherein an extraction area of the container is configured as a cylindrical nozzle.

5. The device according to claim 1, wherein a cap with a diaphragm provided on a base can be fitted onto the connecting piece, wherein the cap is latched in a sleeve-like receptacle in the inserted state.

6. The device according to claim 1, wherein the inner part has another lower receptacle in a lower region for a hub integration of the needle tube.

7. The device according to claim 1, wherein a hub integration for the needle tube is integrated in detent positions in a receptacle.

* * * * *